United States Patent [19]
Cambier et al.

[11] Patent Number: 5,843,070
[45] Date of Patent: Dec. 1, 1998

[54] SIMULATING CORNEAL LASER SURGERY

[75] Inventors: James L. Cambier, Rome, N.Y.;
George W. Rozakis, Lakewood, Ohio

[73] Assignee: ParTech, Inc., New Hartford, N.Y.

[21] Appl. No.: 645,100

[22] Filed: May 13, 1996

[51] Int. Cl.⁶ ..................................................... A61M 5/06
[52] U.S. Cl. ..................................................... 606/5; 606/4
[58] Field of Search .................................. 606/4, 5, 6, 10, 606/11, 12

[56] References Cited

U.S. PATENT DOCUMENTS

| | | | |
|---|---|---|---|
| 4,669,466 | 6/1987 | L'Esperance . | |
| 4,911,711 | 3/1990 | Telfair et al. ................................ | 606/5 |
| 4,995,716 | 2/1991 | Warnicki et al. ........................ | 351/212 |
| 5,098,426 | 3/1992 | Sklar et al. .................................. | 606/5 |
| 5,159,361 | 10/1992 | Cambier et al. ........................ | 351/212 |
| 5,261,822 | 11/1993 | Hall et al. ................................ | 434/271 |
| 5,395,356 | 3/1995 | King et al. .................................. | 606/4 |
| 5,455,766 | 10/1995 | Scheller et al. .......................... | 606/4 X |
| 5,569,238 | 10/1996 | Shei et al. .................................. | 606/4 |
| 5,620,436 | 4/1997 | Lang et al. .................................. | 606/4 |
| 5,642,287 | 6/1997 | Sotiropoulos et al. .................. | 606/5 X |

OTHER PUBLICATIONS

Belin, Michael W.; Cambier, James L.; and Nabors, John R.; "PAR Corneal Topography System"; *Corneal Topography: The State of the Art*; Gills, J. et al., editors; Slack, Inc.; Thorofare, NJ; ch. 8, pp. 105–122; 1995.

Belin, Michael W.; Cambier, James L.; Nabors, John R.; and Ratliff, C. Derek; "PAR Corneal Topography System (PAR CTS): The Clinical Application of Close–Range Photogrammetry"; Opt. Vis. Sci.; 72(11): pp. 828–837; 1995.

El Hage, Sami G.; Salz, James J.; Belin, Michael W.; Costin, John A.; and Gressel, Michael G.; "Corneal Topography as Measured by the EyeMap EH–270"; *Corneal Topography*; chapter 4, pages 37–52; 1995.

Gottsch, John D.; Rencs, Erik V.; Cambier, James L.; Hall, Deborah; Azar, Dimitri T.; and Stark Walter J.; "Excimer Laser Calibration System"; Journal of Refractive Surgery; vol. 12, pp. 401–411; Mar./Apr. 1996.

Munnerlyn, Charles R.; Koons, Stephen J.; and Marshall, John; "Photorefractive Keratectomy: A Technique fo Laser Refractive Surgery"; Journal of Cataract Refractive Surgery; vol. 14, pp. 44–52; Jan., 1988.

PAR Vision Systems Corporation; "CTS™ Corneal Topography System is More Than Meets the Eye".

Rozakis, George W.; "Lasear Simulation Software: Mastering the Response of the Cornea"; Ocular Surgery News; Jul. 15, 1995; pp. 48–49.

Smolek, Michael K. and Klyce, Stephen D.; "The Tomey Technology/Computed Anatomy TMS–1 Videokeratoscope"; *Corneal Topography: The State of the Art*; Gills, J. et al., Slack, Inc.; ch. 9, pp. 124–149; 1995.

(List continued on next page.)

*Primary Examiner*—Robert L. Nasser
*Attorney, Agent, or Firm*—Fish & Richardson P.C.

[57] ABSTRACT

An apparatus and method are provided for simulating a predicted post-operative topography of a cornea of an eye based on a pre-operative topography of the cornea and a proposed laser ablation procedure. A digital data processing system receives data defining a pre-operative topography of the cornea as a function of location and obtains parameters of the proposed laser ablation procedure from which the digital data processing system can determine the amount of cornea expected to be ablated as a function of location on the cornea. Based on the data and the parameters, the digital data processing system produces an output representing a simulated post-operative topography of the cornea as a function of location. The parameters of the proposed laser ablation procedure specify variations in a cut rate of the laser beam (such as data specifying a plurality of laser beam cut rates for each of a corresponding plurality of laser beam pulses, or data specifying relative laser beam energy level or fluence at each of a plurality of points within the laser beam).

25 Claims, 7 Drawing Sheets

OTHER PUBLICATIONS

Snook, Richard K.; "Pachymetry and True Topography Using the ORCAN System"; *Corneal Topography: The State of the Art*; Gills, J. et al., editors; Slack, Inc.; Thorofare, NJ; chapter 7, pp. 89–103; 1995.

Thornton, Spencer P. and Wakil, Joseph; "The EyeSys 2000 Corneal Analysis System"; *Corneal Topography: The State of the Art*; Gills, J. et al., editors; Slack, Inc.; Thorofare, NJ; chapter 5, pp. 55–75; 1995.

Waring III, George O. et al., "Photorefractive Keratectomy for Myopia Using a 4.5–Millimeter Ablation Zone"; Journal of Refractive Surgery; vol. 11, pp. 170–180; May/Jun. 1995.

SIMULATING CORNEAL LASER SURGERY

BACKGROUND OF THE INVENTION

This invention relates to simulation of a change in topography of a cornea based on a set of input parameters defining laser surgery to be performed on the cornea.

The light-refracting properties of the human eye are largely determined by the shape of the front surface of the cornea, the outer covering of the eye. The cornea acts as a lens, and like a typical simple lens, its focal length is determined by the radius of curvature of its surfaces and the index of refraction of the corneal tissue. Individuals who have myopia, or near-sightedness, have a corneal radius of curvature that is too small, so that the corneal focal length is too short and images are formed some distance in front of the retina. Far-sighted individuals have hyperopia, in which the corneal radius is too large, the focal length is too long, and images are formed behind the retina.

Surgical techniques have been developed that seek to alter the shape of the cornea to correct myopia and hyperopia. One such procedure is photorefractive keratectomy (PRK), in which an ultraviolet laser beam from an excimer laser is used to precisely vaporize corneal tissue to change the corneal shape in a desired manner.

In order to change the surface curvature of a myopic cornea, laser pulses are delivered through an expandable aperture, which starts at a small diameter and gradually increases in size as pulses are delivered. As a result, the greatest ablation depth is achieved in the center of the treatment area, and the least depth at the periphery. This has the effect of increasing the radius of curvature by "flattening" the cornea, and can precisely correct the myopia through proper selection of parameters such as aperture sizes, the number of laser beam pulses to be delivered at each aperture size, and the laser "cut rate," which is the depth of tissue to be removed by each pulse.

SUMMARY OF THE INVENTION

One aspect of the invention features an apparatus and method for simulating a predicted post-operative topography of a cornea of an eye based on a pre-operative topography of the cornea and a proposed laser ablation procedure. A digital data processing system receives data defining a pre-operative topography of the cornea as a function of location and obtains parameters of the proposed laser ablation procedure from which the digital data processing system can determine the amount of cornea expected to be ablated as a function of location on the cornea. Based on the data and the parameters, the digital data processing system produces an output representing a simulated post-operative topography of the cornea as a function of location.

Because the simulated post-operative topography is based on a pre-operative topography of the cornea that includes measured elevation as a function of location, the invention provides an accurate simulation in cases in which the pre-operative cornea is irregular due to disease or previous surgical procedure and does not have a pre-operative shape that can be accurately described by a sphero-cylindrical model.

Another aspect of the invention features an apparatus for simulating a predicted change in topography of a cornea of an eye based on parameters of a proposed laser ablation procedure that specify variations in a cut rate of the laser beam (such as data specifying a plurality of laser beam cut rates for each of a corresponding plurality of laser beam pulses, or data specifying relative laser beam energy level or fluence at each of a plurality of points within the laser beam). A digital data processing system obtains the parameters of the proposed laser ablation procedure, from which the digital data processing system can determine the amount of cornea expected to be ablated as a function of location on the cornea, and, based on the parameters, produces an output representing a simulated change in topography of the cornea as a function of location.

Because the simulated change in topography is based on data specifying variations in the cut rate of the laser beam, rather than data specifying a constant cut rate, the simulated change in topography can be highly accurate even if the cut rate of the laser beam is not very accurate or consistent or even if the energy distribution within the laser beam is non-uniform.

Numerous other features, objects, and advantages of the invention will become apparent from the following detailed description when read in connection with the accompanying drawings.

DETAILED DESCRIPTION

Figure 1:
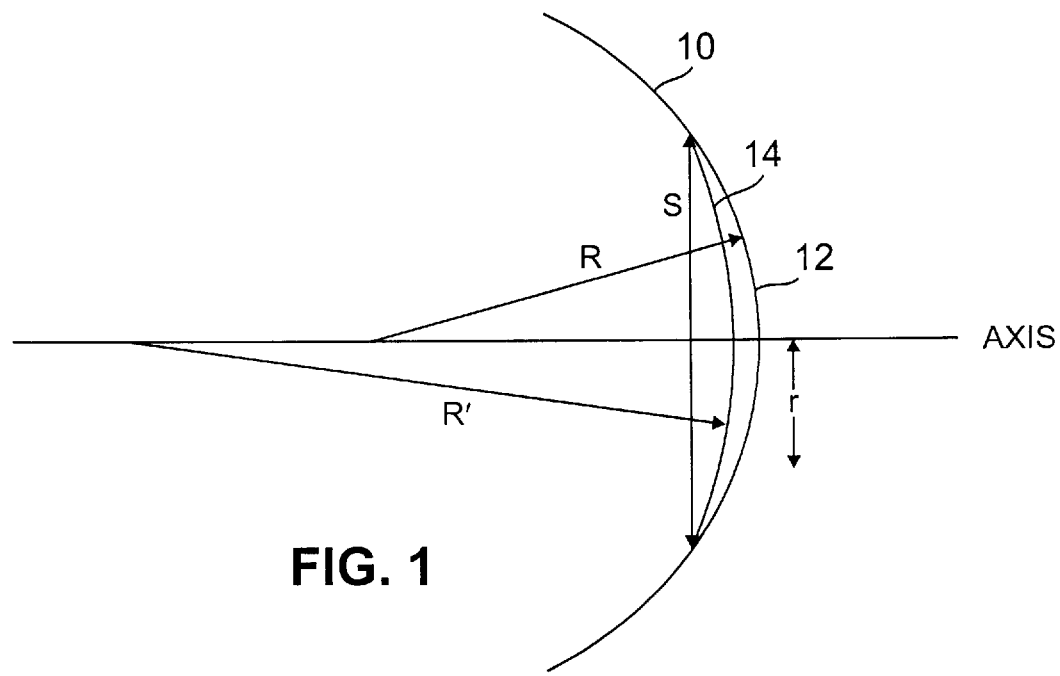
FIG. 1 is a cross-sectional diagram of an eyeball illustrating a region of tissue that is ablated to correct for myopia.

With reference to FIG. 1, eyeball 10 has corneal surface 12 prior to photorefractive keratectomy surgery and surface 14 after the surgery.

The ability of the cornea, or other lenses, to modify the direction of a ray of light that strikes its surface can be characterized as its refractive power, which may be measured in diopters. If a particular lens has a focal length of f (measured in meters) then its refractive power is simply:

$$D = 1/f$$

where D is measured in diopters. For rays of light close to the optical axis of the system, the refractive power in diopters can be calculated as:

$$D = (n-1)/R$$

where n is the index of refraction of cornea tissue (typically 1.3375) and R is the radius of curvature of the lens in meters. If the pre-operative radius of curvature R of the cornea (shown in FIG. 1 above) is known, as well as the number of diopters ΔD of correction required (which would be negative in the case of myopia), then:

$$D + \Delta D = (n-1)/R + \Delta D = (n-1)/R'$$

and the desired post-operative radius of curvature R' (shown in FIG. 1 above) can be calculated as:

$$R' = 1/[1/R + \Delta D/(n-1)].$$

With the pre-operative and post-operative radii of curvature R and R' known, one can calculate the amount of tissue that must be removed as a function of the radial distance out from the center, or apex, of the cornea. As is well known in the art, the thickness of tissue t removed may be calculated as:

$$t(r)=(R^2-r^2)^{1/2}-(R'^2-r^2)^{1/2}-(R^2-S^2/4)^{1/2}+(R'^2-S^2/4)^{1/2}$$

where R is the pre-operative radius of curvature, R' is the post-operative radius of curvature, S is the diameter of the ablation zone, n is the index of refraction (typically 1.3375), and r is the radial distance from the center of the ablation zone. Substituting for R':

$$t(r)=(R^2-r^2)^{1/2}-\{[(R(n-1)/(n-1+R\Delta D)]^2-r^2\}^{1/2}-(R^2-S^2/4)^{1/2}+\{[(R(n-1)/(n-1+R\Delta D)]^2-S^2/4\}^{1/2}.$$

Figure 2:
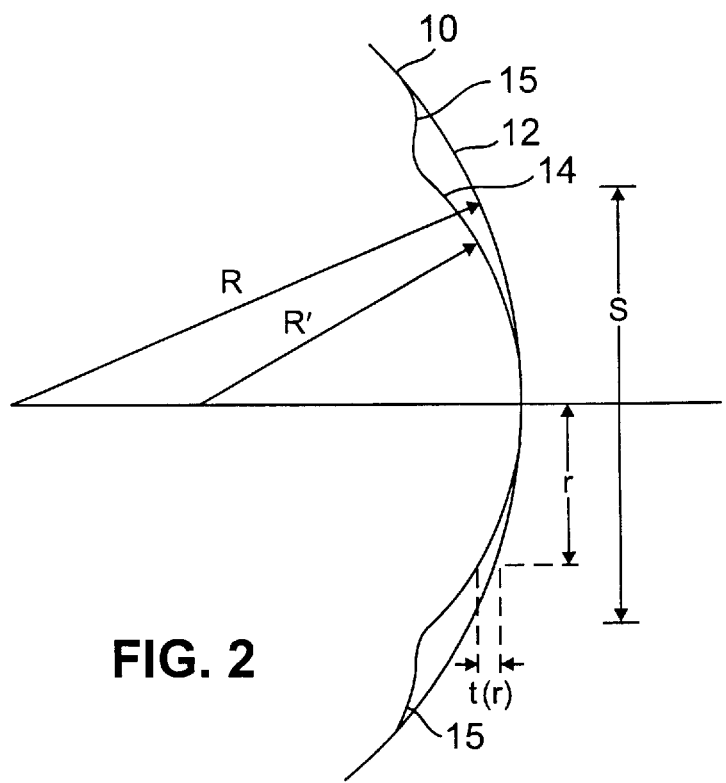
FIG. 2 is a cross-sectional diagram of an eyeball illustrating a region of tissue that is ablated to correct for hyperopia.

A similar equation may be defined for correction of hyperopia, where the central radius of curvature must be increased. In the case of hyperopia:

$$t(r)=(R^2-r^2)^{1/2}-(R'^2-r^2)^{1/2}-(R-R') \text{ for } r<S/2$$

where $$R'=1/[1/R+\Delta D/(n-1)]$$

as before. In this case, as shown in FIG. 2, the ablation produces a discontinuity or "step" at the edge of the ablation zone (which has a diameter equal to S). A "transition zone" 15 is usually created at the edge of the ablation zone that creates a smooth profile that blends into the peripheral surface.

In addition, it is possible to mathematically define additional ablation patterns required to correct corneal astigmatism, in which the radius of curvature of the pre-operative cornea varies along a particular meridian according to the angle of the meridian. Hence, the thickness of tissue removed at a given point is a function of radial distance and the angle of the meridian on which the point lies. For astigmatism combined with myopia, for example:

$$t(r,\Theta)=(R(\Theta)^2-r^2)^{1/2}-(R'(\Theta)^2-r^2)^{1/2}-(R(\Theta)^2-S^2/4)^{1/2}+(R'(\Theta)^2-S^2/4)^{1/2}$$

where $\Theta$ is the meridian angle between 0° and 180°, with 0° corresponding to a horizontal line. $R'(\Theta)$ can be represented in terms of the pre-operative radius and desired correction, where both the radius and correction are now functions of $\Theta$:
$R'(\Theta)=1/[1/R(\Theta)+\Delta D(\Theta)/(n-1)]$.

The above analysis serves to establish that for a particular desired correction, it is possible to mathematically specify the amount of tissue that the laser should attempt to ablate at each point on the surface of the cornea. In particular, the standard approach to ablation for correction of myopia begins by delivering pulses through a small aperture at the center of the optical zone of the eye, and delivering succeeding pulses through a gradually expanding aperture so that the greatest extent of ablation is in the center of the optical zone. It is possible to develop precise algorithms which, based on the parameter t(r) (which is in turn based on the parameters R, $\Delta D$, S, and n as set forth above), the parameter C (average cut rate of the ablation laser, typically 0.25 microns of tissue removed per pulse), and the parameter $\Delta D$ (diameter increment between successive laser aperture sizes, typically 0.1 millimeters), specify the number of pulses to be delivered at each aperture size to obtain the ablation patterns specified by the above equations for t(r). Such an algorithm can be based on the ideal assumptions that the cut rate is very accurate and consistent, that the energy distribution within the laser beam is uniform, and that the pre-operative cornea has a shape that can be accurately described by a sphero-cylindrical model.

For example, one such algorithm specifies i(X,Y), which is the number of the first pulse to be delivered at the point (X,Y), and thus is also the number of pulses delivered at all aperture sizes small enough to prevent any energy from reaching the point (X,Y) plus 1, as follows:

$$i(X,Y) = \left\{ \sum_{k=0}^{P(X,Y)} ([t(r_k)-t(r_{k+1})]/C \right\} + 1$$

where $r_k=r_0+k\Delta d/2$ ($r_k$ being the radius of the kth aperture setting, $r_0$ being the radius of the smallest aperture setting, and $\Delta d$ being the diameter increment between successive laser aperture sizes), where C is the average cut rate of the ablation laser, and where P(X,Y) is the greatest integer less than $2\{[(X-X_C)^2+(Y-Y_C)^2]^{1/2}-r_0\}/\Delta d$ ($X_C$ and $Y_C$ being the coordinates of the center of the ablation zone). In other words, P(X,Y) is simply the sequence number of the greatest aperture size that prevents any energy from reaching the point (X,Y), and i(X,Y) is simply the summation of the number of laser pulses delivered at each aperture size that prevents any energy from reaching the point (X,Y). It can be seen from the above equation that the total number of pulses N to be delivered to the cornea is equal to $i(\hat{X}, \hat{Y})$ where $(\hat{X}, \hat{Y})$ is a point immediately outside the ablation zone, at which t(r) is zero, or in other words:
$N=t(r_0)/C$.

Typically, the ablation procedure starts with a minimal aperture diameter of $2r_0$, and increases in fixed increments up to the largest setting, which determines the overall diameter of the ablation pattern. This particular approach, in which the total ablation depth at a given point is summed up from a series of successive pulses, does not take into account variations in beam intensity or cut rate.

Figure 3:
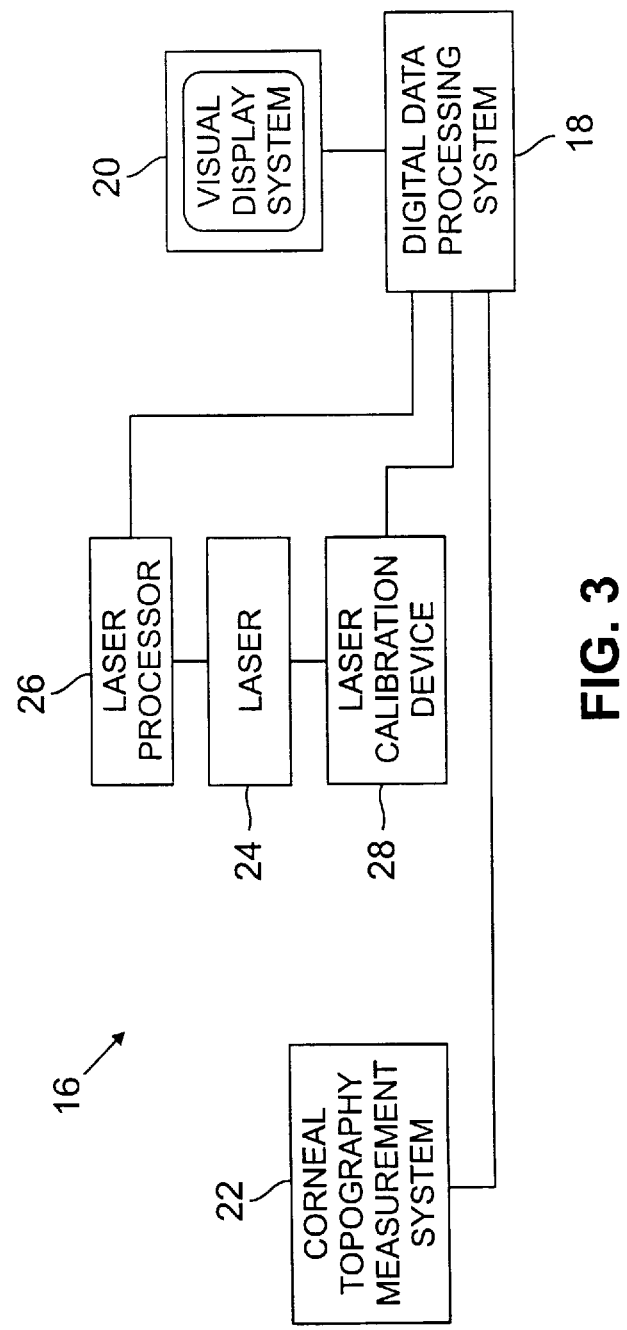
FIG. 3 is a block diagram of a system for simulating a predicted post-operative topography of a cornea in accordance with the invention.

With reference to FIG. 3, there is shown a system 16 that calculates the predicted post-operative topography of the cornea regardless of the pre-operative topography, the system including a digital data processing system 18, a visual display system 20 for displaying pre-operative topography of the cornea together with a simulated post-operative topography generated by the digital data processing system, a corneal topography measurement system 22 for providing to digital data processing system 18 the measured pre-operative elevation of the cornea as a function of location, a laser 24 for ablating the tissue, a laser processor 26 for operating laser 24, and a laser calibration device 28 for measuring the cut rates of successive laser pulses and the relative energy level or fluence of the laser beam at different points within the beam.

In one embodiment, digital data processing system 18 receives from the user the parameters R, $\Delta D$, S, and n and receives from the laser manufacturer the parameters C and $\Delta d$ (although n is typically 1.3375, the appropriate value of n to be supplied by the user may vary somewhat from this value depending on the amount of optical correction required). The digital data processing system uses precise mathematical or tabular specifications of a laser ablation protocol or algorithm, such as, for example, the formulae for i(X,Y) and N set forth above that assume a constant cut rate C and a uniform energy distribution within the laser beam.

The digital data processing system determines the parameter t(r) from the parameters R, ΔD, S, n, and determines i(X,Y) and N from the parameters t(r), C, and Δd, in accordance with formulae such as those set forth above. Alternatively, digital data processing system 18 transmits some or all of the parameters R, ΔD, S, n to laser processor 26, which determines independently of digital data processing system 18 some or all of the parameters t(r), i(X,Y), and N (this eliminates possible duplication, and provides flexibility whereby digital data processing system 18 can be connected to numerous different laser processors 26 that utilize numerous different laser ablation protocols or algorithms for operating laser 24 that may differ from the specific formulae for t(r), i(X,Y), and N set forth above). Alternatively, digital data processing system can receive from the laser manufacturer the values of i(X,Y) and N for various sets of input parameters R, ΔD, S, and n.

The digital data processing system also receives, from laser calibration device 28 or from the laser manufacturer, data defining the predicted average cut rate $C_n$ of the nth laser beam pulse in the series of pulses of the ablation procedure, and the relative fluence F(X,Y) of the laser beam at point (X,Y) on the surface of the cornea that is within the beam. The fluence pattern does not substantially change as the aperture expands. $C_n$ may be constant or may vary from pulse to pulse due to heating effects of the laser. Laser calibration device 28 can be, for example, the LabLight instrument described in Hall et al., U.S. Pat. No. 5,261,822.

Digital data processing system 18 also receives, from corneal topography measurement system 22, a pre-operative topographic model of the cornea composed of direct, point-by-point measurements of surface elevation. The corneal topography measurement system can be, for example, the PAR CTS (Corneal Topography System) described in Warnicki et al., U.S. Pat. No. 4,995,716 and Cambier et al., U.S. Pat. No. 5,159,361, the entire disclosures of which are hereby incorporated herein by reference. The corneal topography measurement system can alternatively be a placido ring device or a scanning slit device capable of generating accurate elevation data or measurements.

Digital data processing system 18 calculates the post-operative height of each point on the cornea by subtracting from the pre-operative height at that point the thickness of tissue to be removed by each laser pulse, taking into account the number of pulses delivered to the particular point, the variation (if any) in energy from one pulse to the next, and the relative energy level or fluence of the portion of the beam that produces the ablation at the point in question. The equation for the computed post-operative elevation Z'(X,Y) is:

$$Z'(X,Y) = Z(X,Y) - \sum_{n=i(X,Y)}^{N} C_n F(X,Y)$$

where Z'(X,Y) is the post-operative elevation at location (X,Y), Z(X,Y) is the pre-operative elevation at location (X,Y) (from corneal topography measurement system 22), N is the total number of laser pulses delivered, i(X,Y) is the number of the first pulse that delivers energy to location (X,Y) (i.e., the number of pulses delivered with the aperture diameter setting less than $2[(X-X_C)^2+(Y-Y_C)^2]^{1/2}$, plus one, where $(X_C,Y_C)$ are the coordinates of the center of ablation), F(X,Y) is the relative fluence of the laser beam at point (X,Y) on the cornea surface, and $C_n$ is the predicted average cut rate of the nth laser pulse.

The above description is appropriate for an ablation pattern designed to correct myopia. In the case of hyperopia, it is desirable to create a central area with a radius of curvature smaller than the pre-operative cornea by ablating the peripheral tissue only, leaving the very center unchanged. This is achieved by masking the central cornea in some manner (for example, using an erodible mask) or by using a small circular or rectangular laser beam that can be applied to the peripheral cornea in a predetermined pattern to produce the desired curvature change. Similarly, astigmatism is corrected by aligning a rectangular aperture with its long axis coincident with the axis of steepest curvature, and by applying laser pulses as the width of the aperture is varied in a predetermined pattern. The length of the aperture may be kept constant while the width is varied, and the number of pulses at each aperture setting typically decreases as the aperture gets wider. In any case, the techniques described above for myopia can be readily adapted to simulate correction of hyperopia and astigmatism, as long as the aperture positions, aperture dimensions, number of pulses for each aperture setting, and laser cut rate are known or can be determined. The appropriate aperture positions and dimensions and the number of pulses to be delivered at each aperture size are known by those skilled in the art can, who are familiar with the laser control algorithms. The laser cut rate can be determined in accordance with the techniques described above.

The excimer laser simulation program, described below, is implemented as a series of software functions of the PAR Corneal Topography System (CTS), which is currently available from PAR Vision Systems Corporation without these additional software functions. The software functions interact with the user to allow input of laser treatment parameters, specification of a pre-operative topography model to be used, and display and archival storage of simulated post-operative topography. The simulated topography can also be further analyzed or measured using PAR CTS (corneal topography system) current software, to calculate curvature or refractive power, simulated keratometric readings, or astigmatic analyses.

The simulated model feature of the simulation program can be broken up into two operations: model creation and model display. The model creation portion deals with the creation process of the simulated model from a pre-op model and the necessary parameters. The model display portion deals with the display of the model after the creation process is completed and the model has been saved. Each of the two portions has unique operations that are described below.

Figure 4:
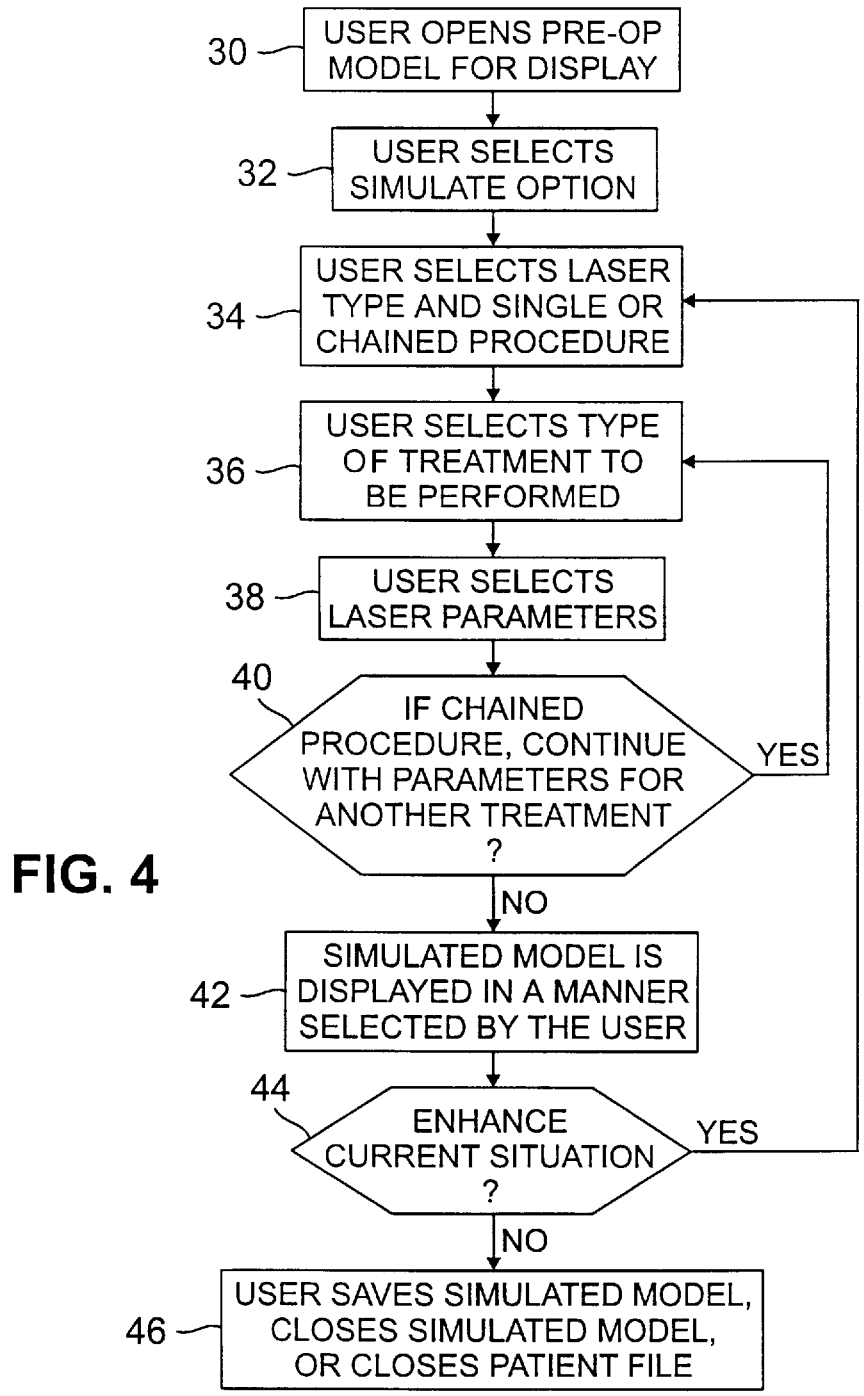
FIG. 4 is a flow-chart diagram illustrating the steps performed by the digital data processing system shown in FIG. 3 during an ablation simulation procedure.
Figure 5:
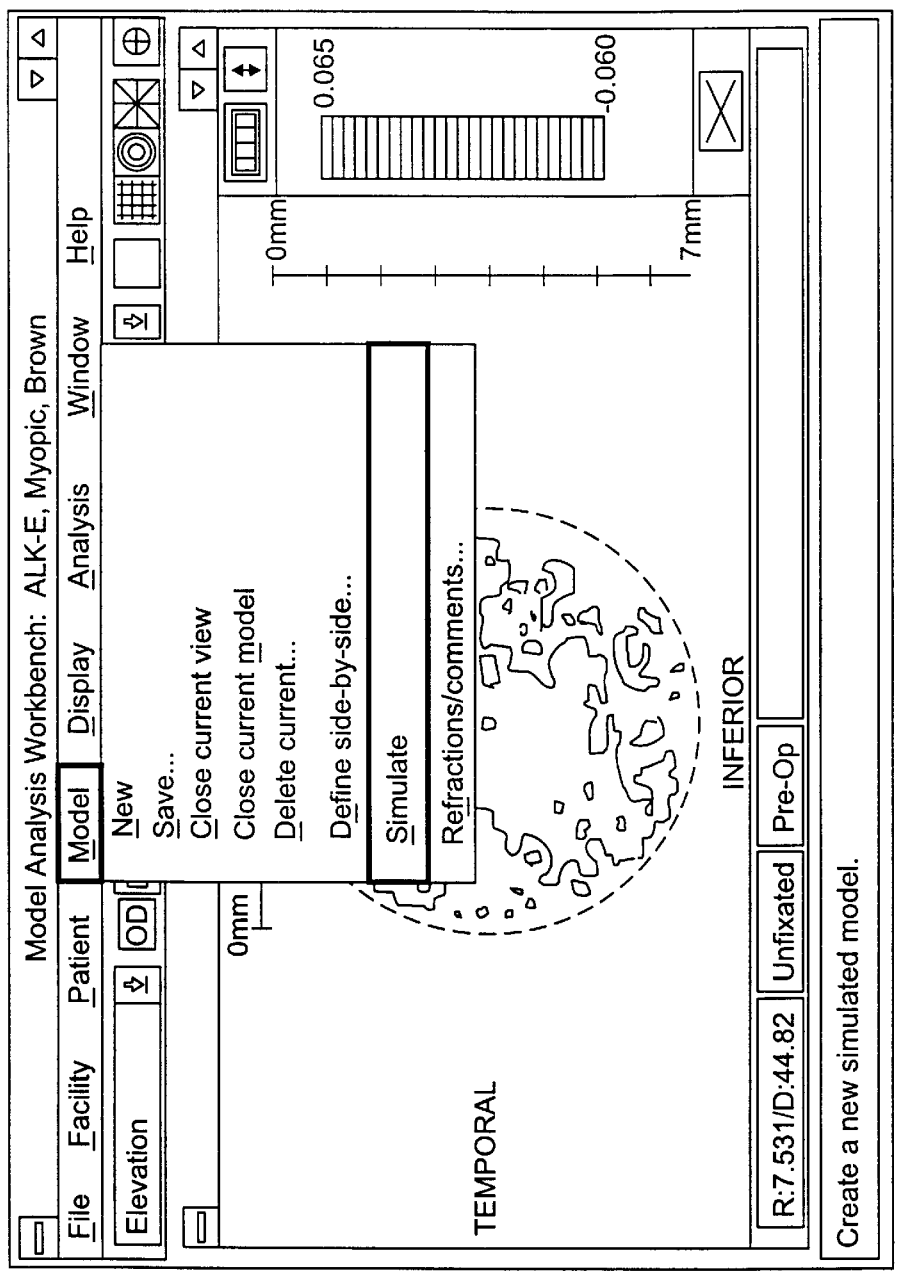
FIGS. 5–9 are screen displays generated by the digital data processing system shown in FIG. 3.

With reference to the flow-chart of FIG. 4 and the screen displays of FIGS. 5–9, in one embodiment of the model creation operation, the user first opens a previously saved pre-op model for display in a Model Analysis Workbench window (step 30) as shown in FIG. 5. The topography of the pre-op model received from the corneal topography measurement system is displayed within the window in a color-coded manner, where each color represents a certain positive or negative deviation from a best-fit sphere, in accordance with the operating procedures of the above-mentioned PAR CTS system, which are known by those skilled in the art. The display mode can be either raw Z, elevation, axial, tangential, refractive power, or side-by-side. If the previously saved pre-op model has the current focus in the window, i.e., the active window on the screen, the user can select a "simulate" option from a menu in the window (step 32) as shown in FIG. 5. In one embodiment the "simulate" option is only available when the window displays a previously saved pre-op model, and is not available when the user is in a difference display or an image display.

Figure 6:
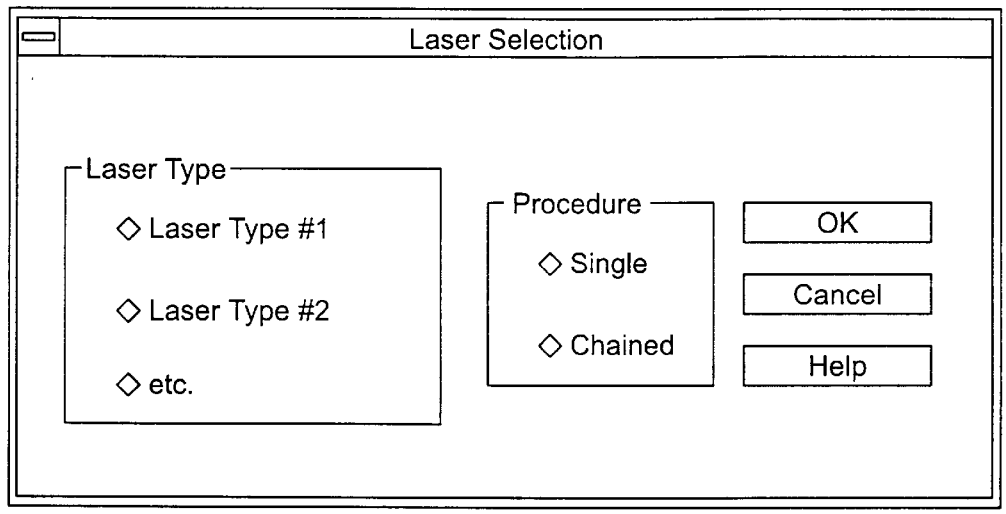

The user is then required to select the type of laser and whether the treatment to be performed is a single procedure or a chained procedure (step 34), as shown in the dialog box of FIG. 6. A single procedure is one that requires only one set of laser method parameters for a single treatment (for example, spherical myopia). A chained procedure is one that requires more than one set of laser method parameters and is used for multiple treatments (for example, spherical myopia followed by astigmatic correction). The default for the type of laser is set in a facility edit window, but the laser type can also be selected from the dialog box shown in FIG. 6. Each laser type is associated with a value of Δd that is known to the digital data processing system.

Figure 7:
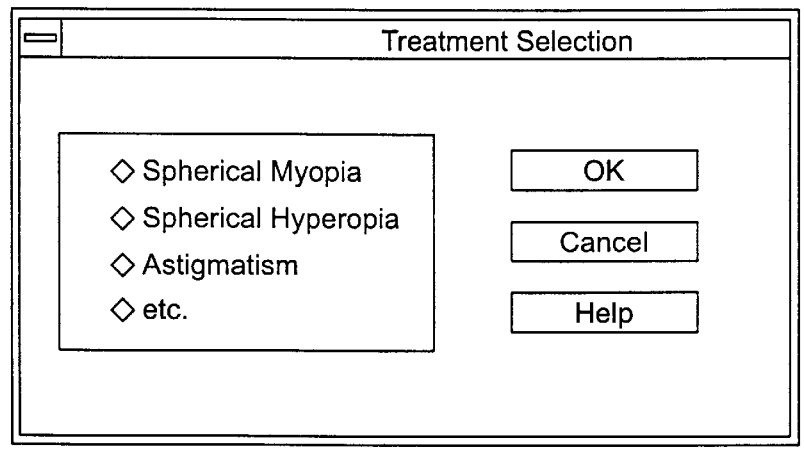

The user is then required to choose the type of treatment to be performed (step 36), as shown in the dialog box of FIG. 7. The types of treatments available may vary depending on the type of laser chosen in the previous dialog box of FIG. 6.

Figure 8:
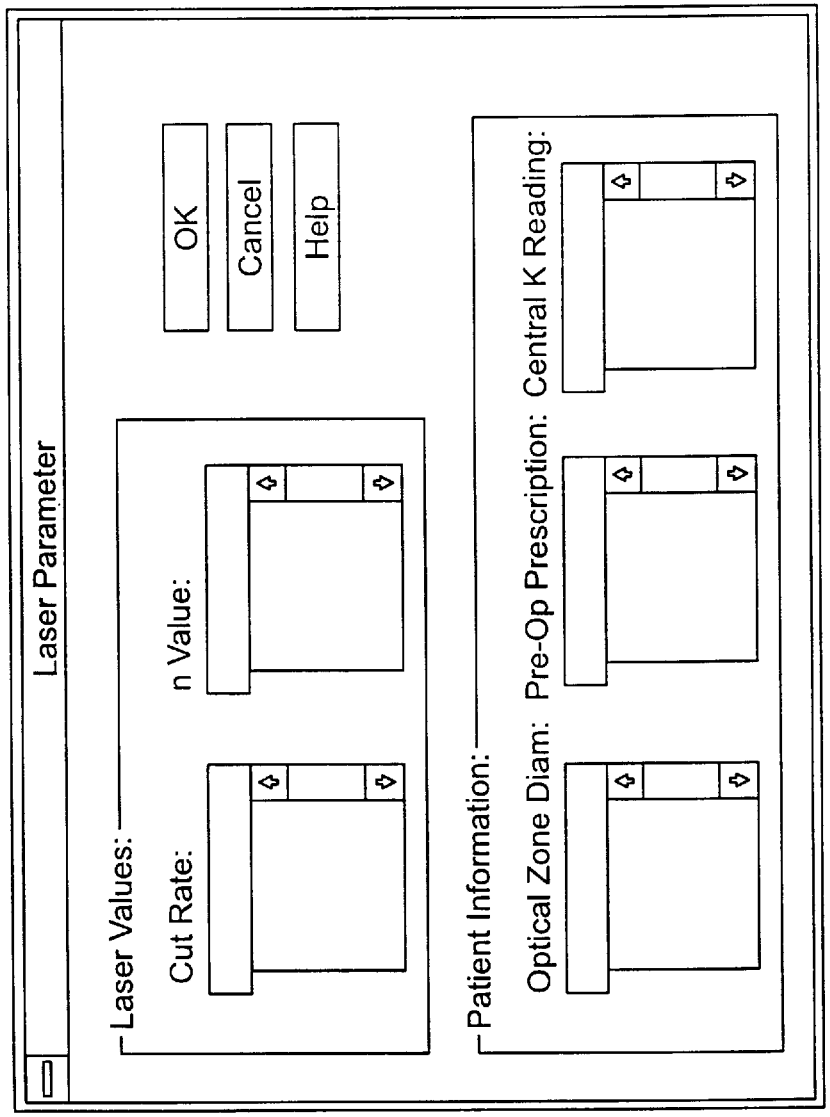

After selecting the appropriate treatment, the user is prompted for the required laser parameters (step 38) with the dialog box shown in FIG. 8. The cut rate corresponds to the parameter C, the n value corresponds to the parameter n, the optical zone diameter corresponds to the parameter S, the pre-op refractive correction prescription corresponds to the parameter ΔD, and the central k reading corresponds to the parameter R according to the formula:

$$k = 337.5/R.$$

If the user selected a chained procedure in the dialog box of FIG. 6, the user is then given the option (step 40) of continuing with the parameters for another treatment or the option of simulating the topography that results from only the first stage in the chain.

In each of the dialog boxes of FIGS. 6–8, the user is given the option of cancelling, which returns the user to the original pre-op display in the Model Analysis Workbench window shown in FIG. 5.

Figure 9:
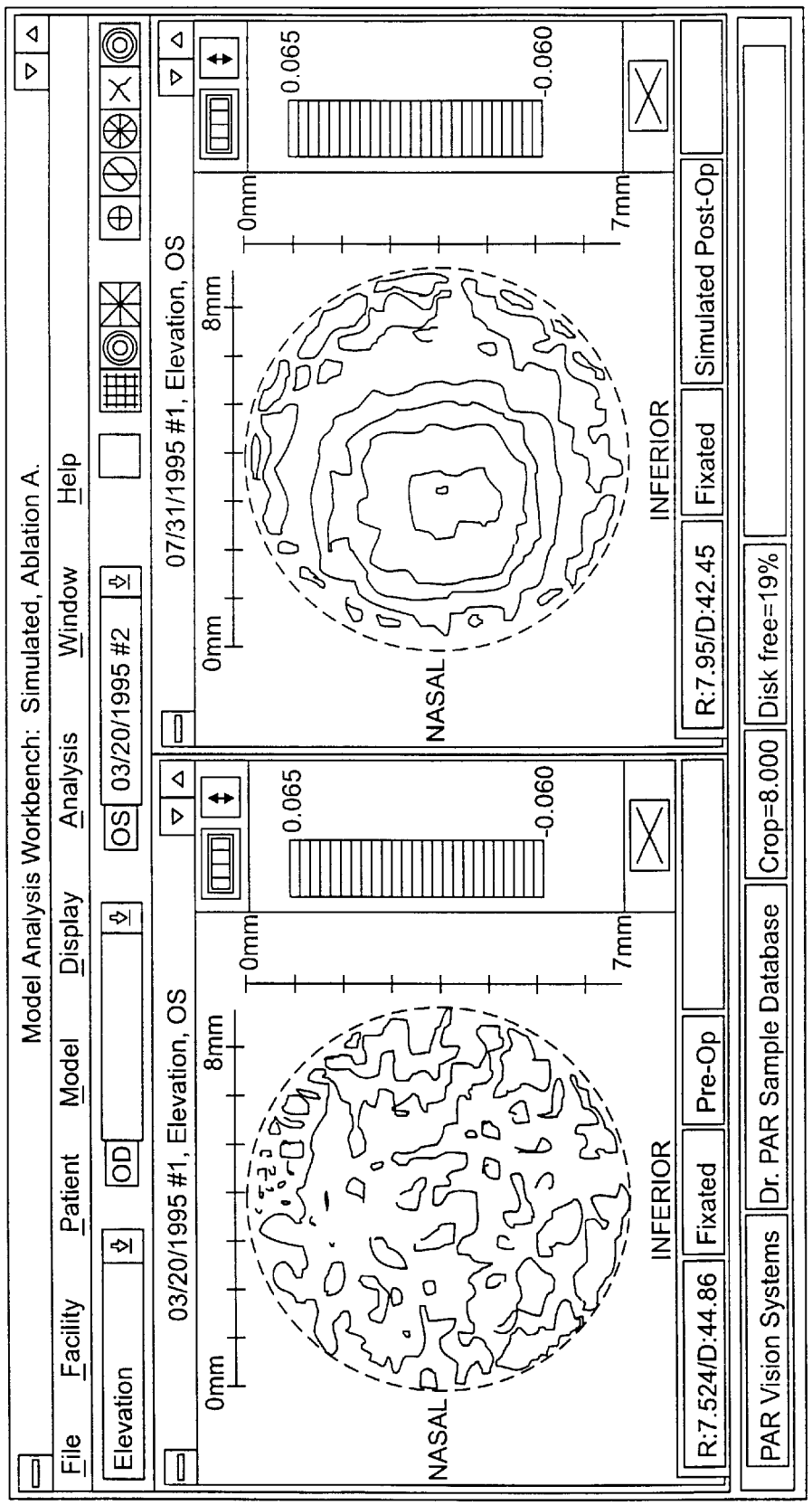

After the digital data processing system creates the simulated model, it is displayed (step 42) in a color-coded manner in the same display mode as the pre-op model (raw Z, elevation, axial, tangential, refractive power). At the option of the user, the simulated model is displayed either as a single display, or side-by-side with any of the following: the pre-op model (as shown in FIG. 9), the pre-op model and the actual post-op model (once a laser procedure has been completed), other simulated models (used primarily for comparison between one simulated surface and a corresponding enhanced simulated surface), the actual post-op model and the difference between the simulated model and the actual post-op model, or the pre-op model and the difference between the simulated model and the pre-op model. At the option of the user, the simulation parameters selected by the user are displayed with the simulated model for reference and will appear on any printout of the simulated model.

As shown in FIG. 9, the display is in the "simulation creation state" with the pre-op model on the left and the simulated model on the right. While the display is in the simulated creation state, the following menu items are disabled: "new model," "image display," and "model open." Other tools and display modes are available, including a "simulation" option (step 44) that allows the user to enhance the current simulation by either editing the parameters previously entered or by adding another treatment to the previous procedure (this option returns the user to one or more of the dialog boxes of FIGS. 6–8). If the "simulation" option is selected, the digital data processing system saves each simulated model together with its parameters. The user can leave the "simulation creation state" (step 46) by saving the simulated model (together with the parameters associated with that model), closing the simulated model, or closing the patient file.

Once the simulated model has been created and saved, the model is no longer in the "simulation creation state." The model can then be displayed in any display mode (except the image mode, because there is no actual image associated with the model) or any display state, including the difference state, which is a state in which the map shows the difference between post-op elevation and pre-op elevation. Any tools can also be applied to the surfaces. When the simulated model is open, any other models for the patient can also be opened with it. Because the model is a simulated model, it is flagged as such in the model analysis workbench window so as not to be confused with actual post-op results. If the simulated model has the current focus, i.e., the active window on the screen, the "simulate" option is disabled.

There has been described novel and improved apparatus and techniques for simulating corneal laser surgery. It is evident that those skilled in the art may now make numerous uses and modifications of and departures from the specific embodiment described herein without departing from the inventive concept.

What is claimed is:

1. An apparatus for producing a simulated post-operative topography model simulating a predicted post-operative topography of a cornea of an eye based on a pre-operative topography of said cornea and a proposed laser ablation procedure, comprising:

a digital data processing system configured to receive data defining a pre-operative topography of said cornea as a function of location, to obtain parameters of said proposed laser ablation procedure from which said digital data processing system can determine the amount of cornea expected to be ablated as a function of location on said cornea, and, based on said data and said parameters, to produce a simulated post-operative topography model representing a simulated post-operative topography of said cornea as a function of location; and a visual display system connected to said digital data processing system for receiving said simulated post-operative topography model from said digital data processing system and for displaying said simulated post-operative topography model of said cornea as a function of location.

2. An apparatus in accordance with claim 1, further comprising a corneal topography measurement system, in communication with said digital data processing system, configured to measure the topography of said cornea as a function of location on said cornea and to produce said data defining said pre-operative topography of said cornea.

3. An apparatus in accordance with claim 1, wherein said digital data processing system comprises means for determining the amount of cornea expected to be ablated as a function of location by internally performing calculations based on said parameters.

4. An apparatus in accordance with claim 1, wherein said digital data processing system comprises means for determining the amount of cornea expected to be ablated as a function of location by receiving from an external processor that operates a laser that performs said laser ablation procedure information pertaining to said amount of cornea expected to be ablated as a function of location.

5. An apparatus in accordance with claim 1, wherein said digital data processing system comprises means for producing said simulated post-operative topography model of said cornea, said means for producing said simulated post-operative topography model comprising means for simulating post-operative elevation of said cornea as a function of location.

6. An apparatus in accordance with claim 5, wherein said digital data processing system comprises means for causing said simulated post-operative elevation of said cornea to be displayed with respect to a best-fit geometric shape.

7. An apparatus in accordance with claim 6, wherein said digital data processing system comprises means for causing said simulated post-operative elevation of said cornea to be displayed with respect to a best-fit geometric shape that comprises a best-fit sphere.

8. An apparatus in accordance with claim 1, wherein said digital data processing system comprises means for causing said simulated post-operative topography model to be displayed in a color-coded manner, where each color represents a certain positive or negative deviation from a geometric baseline.

9. An apparatus in accordance with claim 1, wherein said digital data processing system comprises means for producing said simulated post-operative topography model based on parameters of said proposed laser ablation procedure that comprise a plurality of successive laser beam aperture configurations.

10. An apparatus in accordance with claim 9, wherein said digital data processing system comprises means for producing said simulated post-operative topography model based on parameters of said proposed laser ablation procedure that comprise a number of laser beam pulses to be delivered at each of said laser beam aperture settings.

11. An apparatus in accordance with claim 10, wherein said digital data processing system comprises means for producing said simulated post-operative topography model based on parameters of said proposed laser ablation procedure that comprise a pre-operative radius of curvature of said cornea, and said digital data processing system comprises means for obtaining said number of laser beam pulses to be delivered at each of said laser beam aperture settings by deriving said number from said pre-operative radius of curvature of said cornea.

12. An apparatus in accordance with claim 10, wherein said digital data processing system comprises means for producing said simulated post-operative topography model based on parameters of said proposed laser ablation procedure that comprise a pre-operative refractive correction prescription, and said digital data processing system comprises means for obtaining said number of laser beam pulses to be delivered at each of said laser beam aperture settings by deriving said number from said pre-operative refractive correction prescription.

13. An apparatus in accordance with claim 10, wherein said digital data processing system comprises means for producing said simulated post-operative topography model based on parameters of said proposed laser ablation procedure that comprise a pre-operative optical zone diameter, and said digital data processing system comprises means for obtaining said number of laser beam pulses to be delivered at each of said laser beam aperture settings by deriving said number from said pre-operative optical zone diameter.

14. An apparatus in accordance with claim 10, wherein said digital data processing system comprises means for producing said simulated post-operative topography model based on parameters of said proposed laser ablation procedure that comprise a refraction index of said cornea, and said digital data processing system comprises means for obtaining said number of laser beam pulses to be delivered at each of said laser beam aperture settings by deriving said number from said refraction index of said cornea.

15. An apparatus in accordance with claim 1, wherein said digital data processing system comprises means for producing said simulated post-operative topography model based on parameters of said proposed laser ablation procedure that comprise a laser beam cut rate.

16. An apparatus in accordance with claim 1, wherein said digital data processing system comprises means for producing said simulated post-operative topography model based on parameters of said proposed laser ablation procedure that comprise a plurality of laser beam cut rates for each of a corresponding plurality of laser beam pulses.

17. An apparatus in accordance with claim 1, wherein said digital data processing system comprises means for producing said simulated post-operative topography model based on parameters of said proposed laser ablation procedure that comprise relative laser beam fluence at each of a plurality of points within a laser beam.

18. A method of producing a simulated post-operative topography model simulating a predicted post-operative topography of a cornea based on a pre-operative topography of said cornea and a proposed laser ablation procedure, comprising the steps of:

obtaining from a corneal topography measurement system data defining a pre-operative topography of said cornea as a function of location;

obtaining parameters of said proposed laser ablation procedure;

determining from said parameters the amount of cornea expected to be ablated as a function of location on said cornea; and calculating, based on said pre-operative topography and said amount of cornea expected to be ablated, a simulated post-operative topography model representing a simulated post-operative topography of said cornea as a function of location.

19. A method in accordance with claim 18, further comprising the step of displaying, on a visual display system, said simulated post-operative topography of said cornea as a function of location.

20. An apparatus for simulating a predicted change in topography of a cornea of an eye based on a proposed laser ablation procedure and based on parameters specifying variations in a cut rate of a laser beam, comprising:

a digital data processing system configured to obtain parameters of said proposed laser ablation procedure from which said digital data processing system can determine the amount of cornea expected to be ablated as a function of location on said cornea, and, based on said parameters, to produce an output representing a simulated change in topography of said cornea as a function of location, said parameters specifying variations in a cut rate of a laser beam that ablates said cornea; and a visual display system connected to said digital data processing system for receiving said output of said digital data processing system and for displaying said simulated change in topography of said cornea as a function of location.

21. An apparatus in accordance with claim 20, wherein said digital data processing system comprises means for producing said output representing said simulated change in topography based on parameters specifying variations in a cut rate of said laser beam that comprise a plurality of laser beam cut rates for each of a corresponding plurality of laser beam pulses.

22. An apparatus in accordance with claim 20, wherein said digital data processing system comprises means for producing said output representing said simulated change in topography based on parameters specifying variations in a cut rate of said laser beam that comprise relative laser beam fluence at each of a plurality of points within said laser beam.

23. An apparatus in accordance with claim 20, wherein said digital data processing system comprises means for producing said output representing said simulated change in topography of said cornea, said means for producing said output comprising means for simulating post-operative topography of said cornea.

24. A method of simulating a predicted change in topography of a cornea based on a proposed laser ablation procedure and based on parameters specifying variations in a cut rate of a laser beam, comprising the steps of:

obtaining parameters of said proposed laser ablation procedure, said parameters specifying variations in a cut rate of a laser beam that ablates said cornea;

determining from said parameters the amount of cornea expected to be ablated as a function of location on said cornea; and calculating, based on said amount of cornea expected to be ablated, a simulated change in topography of said cornea as a function of location.

25. A method in accordance with claim 24, further comprising the step of displaying, on a visual display system, said simulated change in topography of said cornea as a function of location.

* * * * *